(12) United States Patent
Paulsen et al.

(10) Patent No.: US 8,616,275 B2
(45) Date of Patent: Dec. 31, 2013

(54) GROUNDWATER EVALUATION TOOLS AND METHODS OF GROUNDWATER EVALUATION

(76) Inventors: Ronald J. Paulsen, Medford, NY (US); David B. Chadwick, San Diego, CA (US); Gregory Jon Groves, San Diego, CA (US); Christopher Smith, Southhold, NY (US)

( * ) Notice: Subject to any disclaimer, the term of this patent is extended or adjusted under 35 U.S.C. 154(b) by 0 days.

(21) Appl. No.: 12/881,588

(22) Filed: Sep. 14, 2010

(65) Prior Publication Data
US 2011/0061473 A1 Mar. 17, 2011

Related U.S. Application Data

(60) Provisional application No. 61/276,717, filed on Sep. 14, 2009.

(51) Int. Cl.
*E21B 23/00* (2006.01)
(52) U.S. Cl.
USPC ............ 166/250.01; 166/64; 175/20; 175/58; 175/319

(58) Field of Classification Search
USPC .............. 175/20–23, 58–59, 314; 73/863, 23, 73/431; 166/250.01, 264, 227
See application file for complete search history.

(56) References Cited

U.S. PATENT DOCUMENTS

| | | | | |
|---|---|---|---|---|
| 6,755,247 | B2 * | 6/2004 | Moake et al. | 166/250.07 |
| 7,311,011 | B2 * | 12/2007 | Clark et al. | 73/864.74 |
| 7,711,489 | B1 * | 5/2010 | Chadwick et al. | 702/12 |
| 2006/0107772 | A1 * | 5/2006 | Shinn et al. | 73/864.43 |

* cited by examiner

*Primary Examiner* — Yong-Suk (Philip) Ro
(74) *Attorney, Agent, or Firm* — Dickstein Shapiro LLP

(57) ABSTRACT

This application is directed to a probe used for measuring groundwater characteristics such as temperature and conductivity, and for collecting a groundwater sample. The probe also has a shielding device that allows the probe to be driven into a hard underwater surface without damaging the probe. A deployment rig for accurately placing the probe into the underwater surface is also disclosed. The application is further directed to a method for placing a probe and measuring groundwater characteristics. An external screen membrane used with the probe allows accurate groundwater characteristic measurement by filtering particulate matter. The probe and external screen membrane allow for in situ measurement and monitoring.

7 Claims, 4 Drawing Sheets

GROUNDWATER EVALUATION TOOLS AND METHODS OF GROUNDWATER EVALUATION

CROSS-REFERENCE TO RELATED APPLICATION

The present application claims the benefit of U.S. Provisional Patent Application No. 61/276,717, filed on Sep. 14, 2009, entitled "Effluent Water Flow Probe, Positioning Rig, Deployment Rig, and Effluent Water Measurement Method," the contents of which is incorporated by reference herein.

FIELD OF THE INVENTION

The present invention relates to groundwater evaluation tools and methods for application in underwater environments.

BACKGROUND OF THE INVENTION

Groundwater evaluation tools, such as conductivity probes, are susceptible to damage when a user places them into an underwater bottom. Accurate measurements are not possible when the groundwater evaluation tools are damaged and measurements become inaccurate or when influenced by direct contact with particulate matter.

A groundwater evaluation tool is disclosed in U.S. Pat. No. 7,711,489. In this known procedure, separate probes, one measuring temperature and the other conductivity, are embedded into a waterbed. A separate sampling system is placed nearby to collect a groundwater sample. However, this bulk measurement system is affected when the sampling tools come into contact with particulate matter in the sediment water or groundwater. For example, the conductivity of the particulate matter will influence this measurement. In addition, when the probes are placed into a hardened underwater bottom such as bedrock, the probes can be severely damaged.

Thus, there is a need for a groundwater evaluation tool that can be placed into a waterbed where the underwater bottom comprises sediment or is hardened without becoming damaged. Additionally, a need exists for a groundwater evaluation tool that is not adversely affected by contact with particulate matter and that can make in situ measurements. Finally, a need exists to be able to accurately place groundwater evaluation tools into an underwater surface and take measurements at a precise location.

SUMMARY OF THE INVENTION

This application is directed to a probe used for measuring groundwater characteristics such as temperature and conductivity, and for collecting a groundwater sample. The probe also has a shielding device that allows the probe to be driven into a hard underwater surface without damaging the probe. A deployment rig for accurately placing the probe into the underwater surface is also disclosed. The application is further directed to a method for placing a probe and measuring groundwater characteristics in situ. An external screen membrane used with the probe allows accurate groundwater characteristic measurement by filtering out particulate and preventing them from entering the reservoir measurement zone around the sensor. The shielded reservoir area allows real time in situ measurements vital to the accurate characterization of the groundwater.

In one embodiment, the application is directed to a liquid tip detection probe for taking measurements in a waterbed, comprising: a drive point adapted for insertion into the waterbed; an elongated body attached to the drive point; a particulate filter removably connected to the elongated body; one or more sensors in the elongated body located within the particulate filter; and a sample tube comprising a first end and a second end, wherein the first end of the sample tube is connected to a sampling system and the second end of the sample tube is located within the particulate filter and proximal to the one or more sensors.

The application is further directed to the liquid tip detection probe for taking measurements in a waterbed where the sensors comprise one or more elements in the group consisting of temperature and conductivity.

The application is further directed to the liquid tip detection probe for taking measurements in a waterbed where the particulate filter comprises a first cylindrical body comprising one or more slots; a screen surrounding the first cylindrical body; and a second cylindrical body surrounding the screen, the second cylindrical body comprising one or more slots.

The application is further directed to the liquid tip detection probe for taking measurements in a waterbed further comprising an armor sheath covering a portion of the elongated body that is inserted into the waterbed.

The application is further directed to the liquid tip detection probe for taking measurements in a waterbed wherein the armor sheath has at least one opening located over the particulate filter.

In yet another embodiment, the application is directed to a liquid tip detection probe comprising means for measuring a groundwater characteristic; means for drawing a groundwater sample; and means for filtering out particulate matter that would interfere with measuring a groundwater characteristic or drawing a groundwater sample.

The application is further directed to the liquid tip detection probe further comprising means for shielding the liquid tip detection from when placed into a waterbed.

In yet another embodiment, the application is directed to a deployment rig, comprising: a submersible deployment frame comprising: a drive rod and an armored liquid tip detection probe; and a deployment system; wherein the armored liquid tip detection probe is adapted to penetrate a waterbed.

The application is further directed to the deployment rig wherein the deployment system is a cable deployment system.

The application is further directed to the deployment rig further comprising a drive weight system that drives the armored probe into the waterbed.

The application is further directed to the deployment rig further comprising a release point mechanism adapted to disconnect the submersible deployment frame from the drive rod.

In yet another embodiment, the application is directed to a method for measuring characteristics of groundwater flowing through a waterbed, comprising: connecting a tube comprising having a first end and a second end located in a liquid tip detection probe to a sampling system at the first end; embedding the liquid tip detection probe into the waterbed; measuring at least one groundwater characteristic; drawing water through the liquid tip detection probe using the sampling system; and collecting a sample of groundwater.

The application is further directed to the method wherein groundwater characteristics comprise at least one of temperature and conductivity.

In yet another embodiment, the application is directed to a detection probe, comprising: an elongated body; one or more sensors in the body; and an external screen membrane removably connected to the elongated body.

The application is further directed to the detection probe where the external screen membrane comprises a reservoir housed in the elongated body; and a plurality of holes along a vertical axis acting as an intake and a conduit for the reservoir.

The application is further directed to the detection probe where the external screen membrane further comprises a filter.

The application is further directed to the detection prober where the external screen membrane further comprises an armor sheath.

The application is further directed to the detection probe wherein the external screen membrane comprises teflon.

BRIEF DESCRIPTION OF THE DRAWINGS

For the purposes of illustrating the present invention, there is shown in the drawings a form which is presently preferred, it being understood however, that the invention is not limited to the precise form shown by the drawing in which.

DETAILED DESCRIPTION OF THE INVENTIONS

Figure 1:
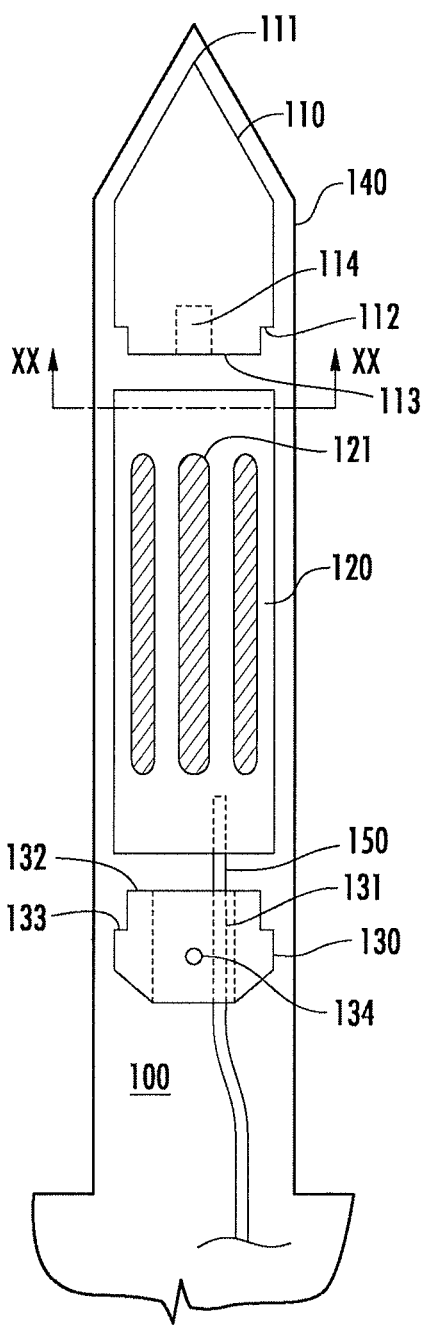
FIG. 1 is a diagram that illustrates a side view of a shield for a probe with an optional armor sheath.

FIG. 1 is a side view diagram that illustrates a shield for a probe with an optional armor sheath. The shield 100 comprises three separate portions: a drive point 110, a filter 120, a top collar 130, and an outer armor 140. Drive point 110 is generally cylindrical and tapers to a point 111. Drive point 110 is preferably made out of a hard metal adapted for driving into an underwater surface or waterbed. Drive point 110 has a hole 114 extending from a bottom surface 113 into drive point 110. Hole 114 is threaded to allow a probe to be screwed into drive point 110 and fixes the probe in relationship to shield 100. Shield 100 serves two important functions. First, it protects the probe 701 from damage when placing it in an underwater surface. Second, it filters out particulate matter from affecting the probe's 701 measurements.

One of the key advantages of the liquid tip detection probe is that it is capable of in situ measurements. The measuring sensors of the probe 702, 703, and 704 (illustrated with three sensors, although any combination of one or more sensors may be used with any particular probe) are located behind filter 120. Filter 120 particulate matter with interfering from the temperature and conductivity measurements being taken by the probe. And even more importantly, a tube 150 drawing a groundwater sample is also located behind filter 120. Thus, instead of taking a bulk measurement, as disclosed in U.S. Pat. No. 7,711,489, an in situ sediment water or groundwater measurement is possible. This ensures that the groundwater sample is taken as close as possible to where the probe is measuring temperature and conductivity.

In an alternative embodiment, when shield 100 is going to be placed in a rock or consolidated bottom, shield 100 can also include outer armor 140. When a probe is being placed in a hardened underwater bottom, shield 100 and a probe 701 can be severely damaged, such that the probe is unusable. In such situations, outer armor 140 should be included. Outer armor 140 is a hard metal device that shield 100 and a probe are positioned in. Outer armor 140 can be attached to submersible deployment frame 501 (illustrated as armored probe 507 in FIG. 5, infra). Outer armor 140 protects both shield 100 and the probe from damage when it is being driven into a hard ground or a hard underwater bottom.

Outer armor 140 also contains openings over filter 120. These openings (not illustrated) allow groundwater to reach the sensors of the probe 702, 703, and 704 and a tube connected to a sampling system 705. The sampling system 705 contains a pump (not illustrated) which draws the groundwater from the area of filter 120 via the tube 150 to where the sample is collected and analyzed. The pump ideally draws a groundwater sample at 10 mL/min, although rates up to 50 mL/min are acceptable.

Figure 2:
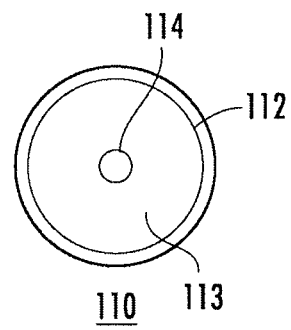
FIG. 2 is a diagram illustrating a cross-sectional view of a base of a drive point for a probe.

FIG. 2 is a cross sectional diagram that illustrates bottom surface 113 of drive point 110 looking upwards from plane xx illustrated in FIG. 1. Upper surface 112 is raised from bottom surface 113 to allow filter 120 to mate with drive point 110.

Filter 120 is a cylindrical, elongated body that preferably has eight slots 121 along a length of filter 120. A sensor portion of a probe 701 is surrounded by filter 120.

Referring back to FIG. 1, top collar 130 is generally cylindrical with a hole 131 all the way through to allow the passage of a probe. The probe 701 fits snugly to the sides of hole 131 to prevent sand, silt, and other like materials from entering into the sensor portion of the probe. Top collar 130 has screw 134 that tightens the top collar 130 to a probe. Lower surface 133 is lowered from top surface 132 to allow top collar 130 to mate with filter 120.

When measuring groundwater characteristics, a user will receive more accurate readings by having the probe submerged into an underwater bottom. Shield 100 allows the probe to be protected and not damaged when inserting the probe in an underwater surface. Additionally, shield 100 and outer armor 140 can be combined to offer further protection to the probe. Oftentimes, an underwater surface will be hard or rocky, such as when it is composed of bedrock. Placing an unprotected probe into that kind of underwater surface could damage the probe and cause it to malfunction. By having shield 100 and outer armor 140 over the probe, damage to the probe can be minimized if not eliminated.

Shield 100 is also designed to allow accurate measurement of groundwater characteristics. Slots 121 allow water to freely flow past the probe sensors so that the shield is not in anyway distorting or preventing accurate measurement of groundwater characteristics. Thus, the benefit of the shield is that it prevents damage to the probe while still allowing accurate measurement of groundwater characteristics.

Figure 3:
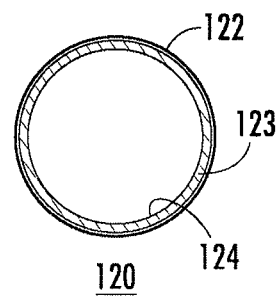
FIG. 3 is a cross-sectional diagram that illustrates a top view of a filter.

FIG. 3 is a cross sectional diagram that illustrates a top view of filter 120. Filter 120 comprises an outer cylindrical surface 122 and an inner cylindrical surface 123. Outer cylindrical surface 122 and inner cylindrical surface 124 both comprise a plurality of slots 121 as shown in FIG. 1. Between outer cylindrical surface 122 and inner cylindrical surface 124 is a screen 123, such as metallic mesh. The mesh size can vary to match the grain size of the particulate matter in the environment in which the shield 100 is to be placed. Outer cylindrical surface 122 has a larger radius than inner cylindrical surface 124 allowing the screen 123 to fit in between. Screen 123 prevents sand, silt, and other like materials from reaching the probe housed within the shield. Water and very fine materials will still pass freely through the screen 123.

Slots 121 of the outer cylindrical surface 122 and the inner cylindrical surface 124 can be aligned to allow maximum flow of water past the sensors of the probe. Alternatively, slots 121 of the outer cylindrical surface 122 can be positioned to partially align with the body of the inner cylindrical surface 124 which cuts off some or all of the flow of water past the sensors of the probe.

Figure 4:
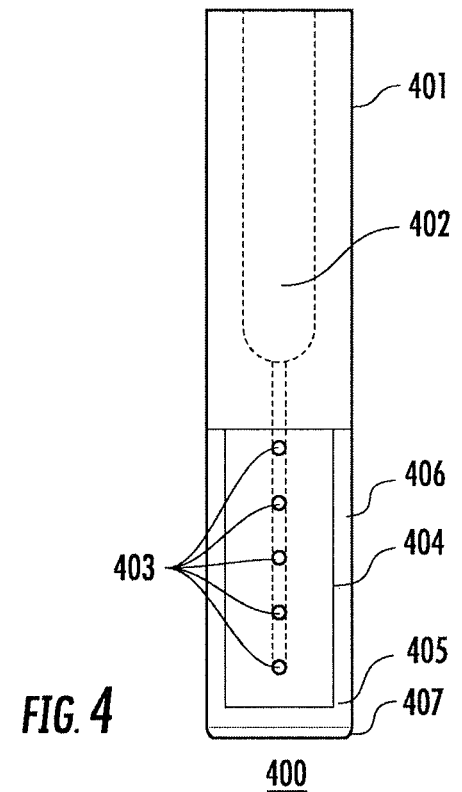
FIG. 4 is a side view that illustrates an external screen membrane.

FIG. 4 is a side view diagram that illustrates an external screen membrane 400. External screen membrane 400 is generally cylindrical. External screen membrane 400 comprises an upper portion 401, a reservoir 402, a lower portion 404, outer screen 406, and screw cap 407. Upper portion 401 has a larger radius than lower portion 404 which allows outer screen 406 to align properly with upper portion 401. Lower portion 404 comprises a plurality of holes along an axis.

External screen membrane 400 is made out of a flexible material, such as teflon. Reservoir 402 holds a probe 701. Water passes through outer screen 406 and into holes 403 which act as an intake and conduit for the reservoir. Any sediment or particulate matter falls out and collects in sediment collection portion 405. Screw cap 407 allows access to the interior of external screen membrane 400 to, for example, remove sediment that has collected in the sediment collection portion 405. Reservoir 402 allows the probe to not be affected by particulate matter and the probe can therefore more accurately gauge groundwater temperature and conductivity.

External screen membrane 400 can also be used with filter 120 (not illustrated in FIG. 4) which is placed over lower portion 404. This reduces the amount of particulate which enters external screen membrane 400. Optionally, outer armor 140 (not illustrated in FIG. 4) may be used to place external screen membrane 400 into an underwater surface.

Figure 5:
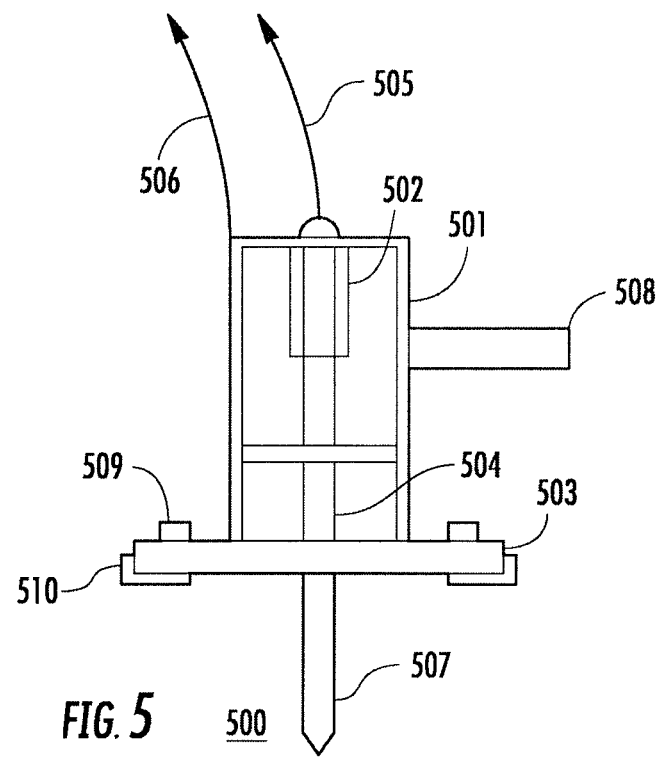
FIG. 5 is a diagram illustrating a side view of a deployment rig.

FIG. 5 is a side view diagram that illustrates a deployment rig 500. Deployment rig 500 comprises a submersible deployment frame 501, a drive weight system 502, a drive rod 504, a deployment system 505, a monitoring system 506, and armored probe 507.

Submersible deployment frame 501 comprises base 503 and stabilizing fin 508. Base 503 comprises weights 509 and mud soft bottom plates 510. Soft bottom plates 510 will rest on the underwater surface when submersible deployment frame 501 is deployed. Weights 509 provide balance to submersible deployment frame 501 as it is being deployed. Stabilizing fin 508 helps to allow the operator to move submersible deployment frame 501 in a controlled fashion as submersible deployment frame 501 is being deployed. Submersible deployment frame 501 is a metal structure designed to be lowered from the surface of a body of water to the underwater surface via deployment system 505. Deployment system 505 is preferably a cable deployment system. Attached to submersible frame 501 is drive weight system 502. Drive weight system 502 is used to drive armored probe 507 into an underwater surface. Drive weight system 502 is preferably either an air hammer or hydraulic system.

Attached to both drive weight system 502 and submersible deployment frame 501 is drive rod 504. Drive rod 504 is a metallic pole system. Drive rod 504 comprises a release point mechanism (not illustrated) that allows the drive rod to disconnect from armored probe 507. The advantage of a release point mechanism is that normally the user's boat needs to be within ten feet of the location of the probe. This can be difficult in a marine environment where a current or wind can move the user's boat away from the location of the probe. By utilizing a release point mechanism, the radius the user can be located in expands. Drive rod 504 also comprises housing that holds the armored probe 507 in place during deployment.

Armored probe 507 is a shielded probe encased in outer armor (illustrated in FIG. 1, supra). When armored probe 507 is to be driven into an underwater surface, armored probe 507 is connected to drive rod 504. Deployment rig 500 is then lowered to the underwater surface using deployment system 505. Drive weight system 502 inserts armored probe 507 into the underwater surface. Monitoring system 506 comprises communication gear allowing the probe to communicate the groundwater characteristics being measured by probe to the surface. Monitoring system 506 also comprises sampling gear that allows a user on the surface of the water to collect a groundwater sample. Armored probe 507 can be left in the underwater surface and deployment rig 500 can be recovered by using the release point mechanism to disconnect the shielded probe from deployment rig 500 and then using the deployment system 505 to recover the deployment rig.

Figure 6:
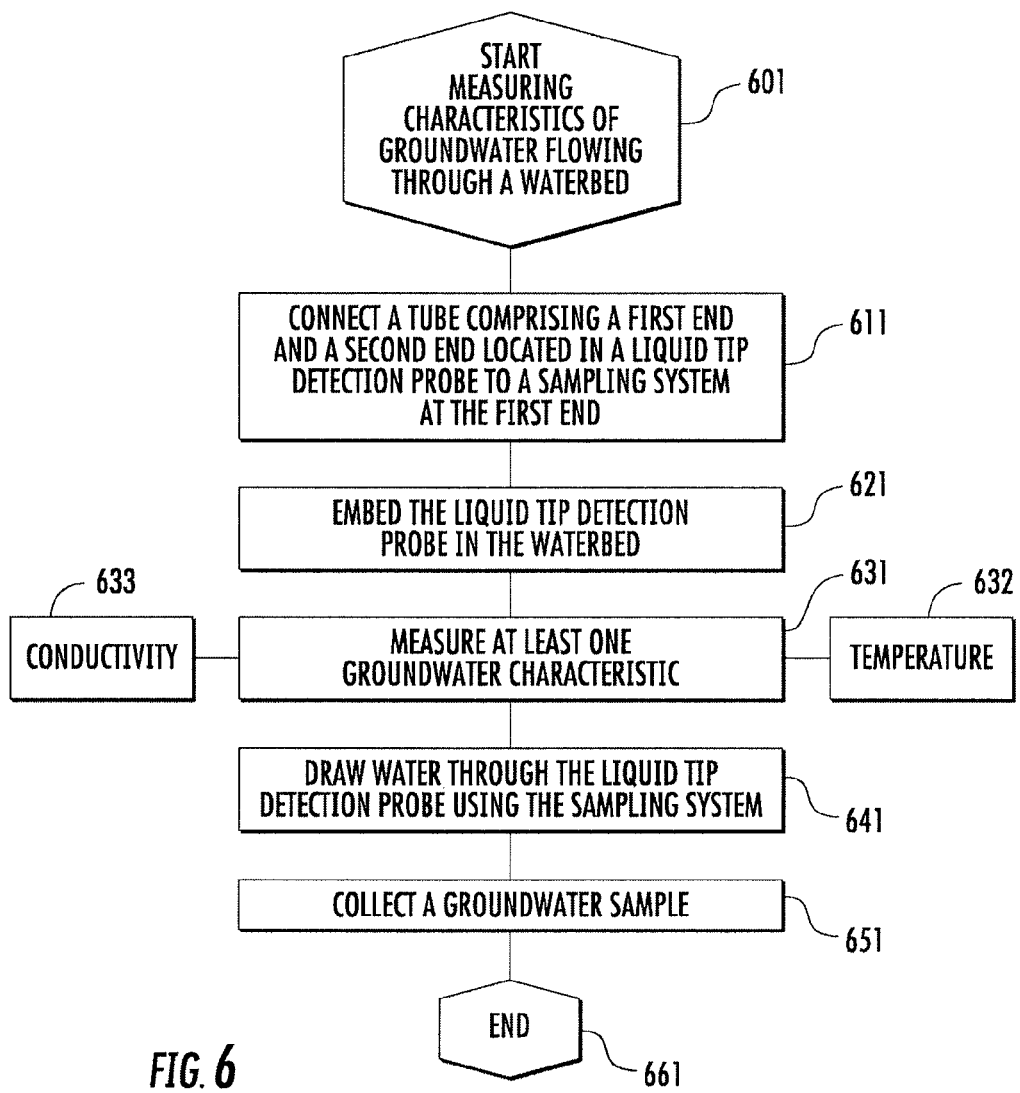
FIG. 6 is a flow chart that illustrates a method for measuring groundwater.
Figure 7:
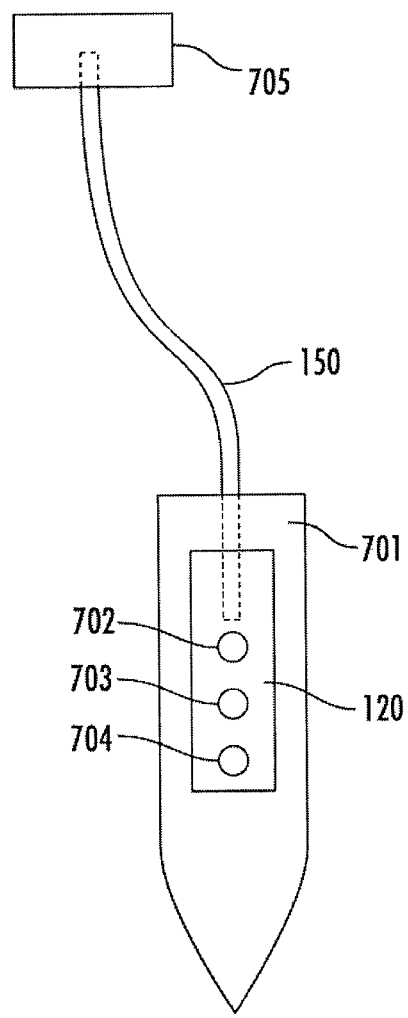
FIG. 7 is a diagram illustrating a probe, one or more sensors, and a sampling system.

FIG. 6 is a flow chart that illustrates a method for measuring groundwater in situ. As illustrated in FIG. 6, in step 601, a user decides to measure a property of groundwater, such as temperature or conductivity, with a liquid tip detection probe. In step 611, the user connects a tube having a first end and a second end located in a liquid tip detection probe to a sampling system at the first end. In step 621, the user embeds the liquid tip detection probe into the waterbed. In step 631, the user measures groundwater characteristics, including temperature 632 and conductivity 633. In step 641, the user draws water through the liquid tip detection probe using a the sampling system. In step 651, the user collects a sample of groundwater.

Measuring temperature and conductivity while drawing a groundwater sample is an important quality control mechanism that ensures the groundwater sample is not tainted by particulate matter. Additionally, groundwater characteristics are continuously monitored in situ during sampling. Thus, this is a superior method of sampling compared to the prior art methods of blind sampling. It is also important to note that the probe is capable of measuring other groundwater characteristics including pH, oxidation reduction potential (ORP), and dissolved oxygen (DO).

Having thus described at least illustrative embodiments of the invention, various modifications and improvements will readily occur to those skilled in the art and are intended to be within the scope of the invention. Accordingly, the foregoing description is by way of example only and is not intended as limiting. The invention is limited only as defined in the following claims and the equivalents thereto.

What is claimed is:

1. A liquid tip detection probe for taking measurements in a waterbed, comprising:
  a drive point adapted for insertion into the waterbed;
  an elongated body attached to the drive point;
  a particulate filter having a top opening, a bottom opening, and a cylindrical surface, the particulate filter being removably connected to the elongated body;
  one or more sensors in the elongated body located between the top opening, the bottom opening, and the cylindrical surface of the particulate filter; and
  a sample tube comprising a first end and a second end, wherein the first end of the sample tube is connected to a sampling system and the second end of the sample tube is located between the top opening, the bottom opening, and the cylindrical surface of the particulate filter and proximal to the one or more sensors.

2. The liquid tip detection probe for taking measurements in a waterbed of claim 1, the sensors comprising one or more elements in the group consisting of temperature and conductivity.

3. The liquid tip detection probe for taking measurements in a waterbed of claim 1, the sensors comprising one or more elements in the group consisting of pH, oxidation reduction potential (ORP), and dissolved oxygen (DO).

4. The liquid tip detection probe for taking measurements in a waterbed of claim 1, the particulate filter comprising:
   a first cylindrical body comprising one or more slots;
   a screen surrounding the first cylindrical body; and
   a second cylindrical body surrounding the screen, the second cylindrical body comprising one or more slots.

5. The liquid tip detection probe for taking measurements in a waterbed of claim 4, wherein the armor sheath has at least one opening located over the particulate filter.

6. The liquid tip detection probe for taking measurements in a waterbed of claim 1, further comprising an armor sheath covering a portion of the elongated body that is inserted into the waterbed.

7. The liquid tip detection probe of claim 1, wherein the sample tube comprises a flexible material.

* * * * *